United States Patent [19]

Smith

[11] 4,010,189

[45] Mar. 1, 1977

[54] ALKANOLAMINE DERIVATIVES

[75] Inventor: Leslie Harold Smith, Macclesfield, England

[73] Assignee: Imperial Chemical Industries Limited, London, England

[22] Filed: Aug. 26, 1975

[21] Appl. No.: 607,995

Related U.S. Application Data

[62] Division of Ser. No. 421,669, Dec. 4, 1973, Pat. No. 3,928,412.

[30] Foreign Application Priority Data

Dec. 15, 1972 United Kingdom ............ 57970/72
Sept. 17, 1973 United Kingdom ............ 43478/73

[52] U.S. Cl. ..................... 260/465 D; 260/79.5 C; 260/470; 260/471 C; 260/501.17; 260/501.18; 260/501.19; 260/557 R; 260/558 A; 260/558 D; 260/558 P; 260/558 S; 260/559 A; 260/559 R; 260/559 T; 260/562 A; 260/562 B; 250/562 P; 260/79.5 NV

[51] Int. Cl.$^2$ .............. C07C 103/82; C07C 121/80; C07C 125/06

[58] Field of Search ....... 260/465 D, 557 R, 558 A, 260/558 D, 558 P, 559 A, 559 R, 562 A, 562 B, 562 P, 470, 471 C, 501.17, 501.18, 501.19, 79.5 R

[56] References Cited

UNITED STATES PATENTS 3,459,782   8/1969   Koppe et al. ...................... 260/465
3,663,607   5/1972   Barrett et al. ................. 260/465 X

*Primary Examiner*—Dolph H. Torrence
*Attorney, Agent, or Firm*—Cushman, Darby & Cushman

[57] ABSTRACT

Novel 1-aryloxy-3-amidoalkylamino-2-propanol derivatives, processes for their manufacture, pharmaceutical compositions containing them and methods of using them in the treatment of heart diseases. The compounds possess β-adrenergic blocking activity and some of them additionally possess cardiac stimulant activity. Representative of the compounds disclosed is 1-phenoxy-3-β-isobutyramidoethylamino-2-propanol.

14 Claims, No Drawings

ALKANOLAMINE DERIVATIVES

This is a division of application Ser. No. 421,669, filed Dec. 4, 1973, now U.S. Pat. 3,928,412.

This invention relates to new alkanolamine derivatives which possess β-adrenergic blocking activity.

According to the invention there is provided a new alkanolamine derivative of the formula:

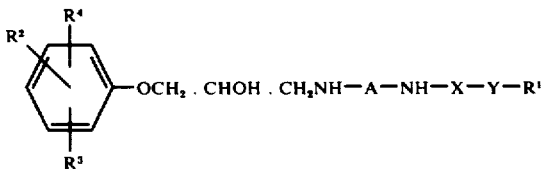

wherein A stands for an alkylene radical of from 2 to 12 carbon atoms; wherein $R^1$ stands for the hydrogen atom or for an alkyl, halogenoalkyl, alkenyl or cycloalkyl radical each of up to 10 carbon atoms, or for an aryl radical of the formula:

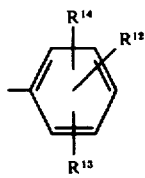

wherein $R^2$, $R^3$, $R^{12}$ and $R^{13}$, which may be the same or different, each stands for a hydrogen or halogen atom, a hydroxy, amino, nitro or cyano radical, an alkyl, cycloalkyl, alkenyl, alkynyl, alkoxy, alkylthio, cycloalkoxy, alkenyloxy, alkynyloxy or alkanoyl radical each of up t 6 carbon atoms, or an aryl, aryloxy or aralkoxy radical each of up to 12 carbon atoms; or wherein $R^2$ and $R^3$ together, and/or $R^{12}$ and $R^{13}$ together, form the trimethylene, tetramethylene, 1-oxotetramethylene, propenylene, but-2-enylene or buta-1,3-dienylene radical such that together with two adjacent carbon atoms of the benzene ring they form respectively the indanyl, 5,6,7,8-tetrahydronaphthyl, 5-oxo-5,6,7,8-tetrahydronaphthyl, indenyl, 5,8-dihydronaphthyl or naphthyl radical; wherein $R^4$ stands for the hydrogen atom or for the hydroxy or hydroxymethyl radical or for an aralkoxy radical of up to 12 carbon atoms; wherein $R^{14}$ stands for the hydrogen atom or for the amino radical or for a dialkylamino radical of up to 12 carbon atoms; wherein X stands for the carbonyl (—CO—) or sulphonyl (—SO$_2$—) radical and wherein Y stands for a direct link, or for an alkylene, oxyalkylene or alkyleneoxy radical each of up to 6 carbon atoms, or for the imino (—NH—) radical, or for an alkylimino, iminoalkylene, iminoalkyleneoxy or iminoalkylenecarbonyloxy radical each of up to 6 carbon atoms, or (except when $R^1$ stands for the hydrogen atom) for the oxygen atom; or an acid-addition salt thereof.

It will be observed that the alkanolamine derivative of the invention possesses an asymmetric carbon atom, namely the carbon atom of the —CHOH— group in the alkanolamine sidechain, and it can therefore exist in racemic and optically-active forms. It is to be understood that this invention encompasses the racemic form of the alkanolamine derivative and any optically-active form which possesses β-adrenergic blocking activity, it being a matter of common general knowledge how a racemic compound may be resolved into optically-active forms, and how the β-adrenergic blocking activity of these forms may be determined. It is further to be understood that β-adrenergic blocking activity usually predominates in that optically-active form which has the S absolute configuration of the said —CHOH— group.

A suitable value for the alkylene radical A is, for example, the ethylene, trimethylene, tetramethylene, hexamethylene, dodecamethylene, 1-methylethylene, 2-methylethylene of 1,1-dimethylethylene radical. A is preferably the ethylene, 1-methylethylene of 1,1-dimethylethylene radical.

A suitable value for $R^1$ when it stands for an alkyl, halogenoalkyl, alkenyl or cycloalkyl radical is, for example, the methyl, ethyl, n-propyl, isopropyl, n-butyl, isobutyl, t-butyl, n-pentyl, n-octyl, trifluoromethyl, allyl, cyclopropyl, cyclopentyl or cyclohexyl radical.

A suitable value for $R^2$, $R^3$, $R^{12}$ or $R^{13}$ when it stands for a halogen atom is, for example, the fluorine, chlorine, bromine or iodine atom.

A suitable value for $R^2$, $R^3$, $R^{12}$ or $R^{13}$ when it stands for an alkyl, cycloalkyl, alkenyl, alkynyl, alkoxy, alkylthio, cycloalkoxy, alkenyloxy, alkynyloxy or alkanoyl radical is, for example, the methyl, ethyl, n-propyl, cyclopropyl, cyclopentyl, allyl, ethynyl, methoxy, isopropoxy, methylthio, cyclopentyloxy, allyloxy, propargyloxy, formyl or acetyl radical.

A suitable value for $R^2$, $R^3$, $R^{12}$ or $R^{13}$ when it stands for an aryl or aryloxy radical is, for example, the phenyl or phenoxy radical.

A suitable value for $R^2$, $R^3$, $R^4$, $R^{12}$ or $R^{13}$ when it stands for an aralkoxy radical is, for example, the benzyloxy radical.

A suitable value for $R^{14}$ when it stands for a dialkylamino radical is, for example, the dimethylamino radical.

A suitable value for Y when it stands for an alkylene, oxyalkylene or alkyleneoxy radical is, for example, the methylene, ethylene, oxymethylene, methyleneoxy, ethyleneoxy, trimethyleneoxy, 1-methylethylideneoxy or 1-methylpropylideneoxy radical.

A suitable value for Y when it stands for an alkylimino, iminoalkylene, iminoalkyleneoxy or iminoalkylenecarbonyloxy radical is, for example, the methylimino, iminomethylene, iminomethyleneoxy or iminomethylenecarbonyloxy radical.

A suitable acid-addition salt of an alkanolamine derivative of the invention is, for example, a salt derived from an inorganic acid, for example a hydrochloride, hydrobromide, phosphate or sulphate, or a salt derived from an organic acid, for example an oxalate, lactate, tartrate, acetate, salicylate, citrate, benzoate, β-naphthoate, adipate or 1,1-methylene-bis-(2-hydroxy-3- naphthoate), or a salt derived from an acidic synthetic resin, for example a sulphonated polystyrene resin.

A preferred alkanolamine derivative of the invention is a compound of the formula given above wherein A stands for the ethylene, 1-methylethylene or 1,1-dimethylethylene radical and wherein either a. $R^1$ stands for the hydrogen atom or for an alkyl, alkenyl or cycloalkyl radical each of up to 6 carbon atoms, or for the trifluoromethyl radical, or for a monohydroxyphenyl or dihydroxyphenyl radical, Y stands for the direct link or for an imino radical, X stands for the carbonyl radical, $R^2$ stands for the hydrogen atom or for a chloro, cyano, nitro, methyl, allyl, methoxy or allyloxy substituent which is in the ortho-position of the benzene ring and $R^3$ and $R^4$ both stand for hydrogen atoms; or b. $R^1$ stands for a phenyl radical, $R^{12}$ stands for the hydrogen atom or for a chloro, nitro, methyl or methoxy substituent, $R^{13}$ and $R^{14}$ both stand for hydrogen atoms, Y stands for the methylene, ethylene, methyleneoxy or imino radical, X stands for the carbonyl radical, $R^2$ stands for the hydrogen atom or for a chloro, cyano, nitro, methyl, allyl, methoxy or allyloxy substituent which is in the ortho- or meta-position of the benzene ring and $R^3$ and $R^4$ both stand for hydrogen atoms; or c. $R^1$ stands for the hydrogen atom or for an alkyl radical of up to 6 carbon atoms, Y stands for the methyleneoxy radical, X stands for the carbonyl radical and $R^2$, $R^3$ and $R^4$ have the meanings stated in paragraph (a) above; or d. $R^1$ stands for an alkyl radical of up to 6 carbon atoms or for a phenyl radical, $R^{12}$ stands for the hydrogen atom or for a chloro, amino, nitro or methyl substituent, $R^{13}$ and $R^{14}$ both stand for hydrogen atoms, Y stands for the direct link, X stands for the sulphonyl radical and $R^2$, $R^3$ and $R^4$ have the meanings stated in paragraph (a) above; or e. $R^1$ stands for an alkyl or cycloalkyl radical each of up to 6 carbon atoms, or for a phenyl radical, $R^{12}$ stands for the hydrogen atom or for a methyl, methoxy or phenyl substituent, $R^{13}$ and $R^{14}$ both stand for hydrogen atoms, Y stands for the direct link or for the methylene or imino radical, X stands for the carbonyl or sulphonyl radical, $R^2$ stands for the hydrogen atom or for the hydroxy radical, $R^3$ stands for the hydrogen atom and $R^4$ stands for the hydroxy radical; or f. $R^1$ stands for an alkyl radical of up to 6 carbon atoms, Y stands for the oxygen atom or for the methyleneoxy, methylimino, iminomethyleneoxy or iminomethylenecarbonyloxy radical, X stands for the carbonyl or sulphonyl radical and $R^2$, $R^3$ and $R^4$ have the meanings stated in paragraph (e) above; or an acid-addition salt thereof.

Specific alkanolamine derivatives of the invention are those hereinafter described in the Examples. Of these, preferred compounds by virtue of their high cardioselective β-adrenergic blocking activity (as hereinafter defined) are:

1-phenoxy-3-β-benzamidoethylamino-2-propanol;
1-phenoxy-3-β-benzenesulphonamidoethylamino-2-propanol;
1-phenoxy-3-β-phenylacetamidoethylamino-2-propanol;
1-phenoxy-3-β-phenoxyacetamidoethylamino-2-propanol;
1-phenoxy-3-β-(3-phenylureido)ethylamino-2-propanol;
1-phenoxy-3-(α-methyl-β-phenylacetamidoethyl)amino-2-propanol;
1-phenoxy-3-β-pivalamidoethylamino-2-propanol;
1-phenoxy-3-(β-isobutyramido-α-methylethyl)amino-2-propanol;
1-(2-nitrophenoxy)-3-β-isobutyramidoethylamino-2-propanol;
1-phenoxy-3-β-propionamidoethylamino-2-propanol;
1-phenoxy-3-β-hydroxyacetamidoethylamino-2-propanol;
1-phenoxy-3-β-(2-nitrobenzenesulphonamidoethyl)amino-2propanol;
1-(2-cyanophenoxy)-3-β-propionamidoethylamino-2-propanol;
1-phenoxy-3-β-isopropylsulphonamidoethylamino-2-propanol;
1-phenoxy-3-β-(2-chlorophenylacetamidoethyl)amino-2-propanol;
1-)2-cyanophenoxy)-3-β-(3-phenylureidoethyl)amino-2-propanol;
1-phenoxy-3-β-butyramidoethylamino-2-propanol;
1-phenoxy-3-β-(3-n-butylureiodoethyl)amino-2-propanol;
1-phenoxy-3-β-isobutyramidoethylamino-2-propanol;
1-phenoxy-3-β-(4-methoxyphenylacetamidoethyl)amino-2-propanol;
1-phenoxy-3-β-acetamidoethylamino-2-propanol;
1-phenoxy-3-β-(n-propylsulphonamidoethyl)amino-2-propanol;
1-(2-methoxyphenoxy)-3-β-isobutyramidoethylamino-2-propanol;
1-phenoxy-3-(α,α-dimethyl-β-isobutyramidoethyl)amino-2-propanol; and
1-phenoxy-3-(α,α-dimethyl-β-phenylacetamidoethyl)amino-2-propanol; and the acid-addition salts thereof.

Preferred compounds by virtue of their high level of cardiac stimulant activity (as hereinafter defined) are:

1-(4-hydroxyphenoxy)-3-β-(3-phenylureido)ethylamino-2-propanol;
1-(3,4-dihydroxyphenoxy)-3-β-isobutyramidoethylamino-2-propanol;
1-(3,4-dihydroxyphenoxy)-3-β-(phenylureido)ethylamino-2-propanol;
1-(3-hydroxphenoxy)-3-β-(3-phenylureido)ethylamino-2-propanol;
1-(3-hydroxyphenoxy)-3-β-benzenesulphonamidoethylamino-2-propanol;
1-(4-hydroxyphenoxy)-3-β-(3,3-dimethylsulphamido)ethylamino-2-propanol;
1-(4-hydroxyphenoxy)-3-β-(3-methoxymethylureido)ethylamino-2-propanol; and
1-(4-hydroxyphenoxy-3-β-(3-n-butyloxycarbonylureido)ethylamino-2-propanol;
and the acid-addition salts thereof.

The alkanolamine derivative of the invention may be manufactured by any chemical process known to be useful for the manufacture of chemically-analogous compounds.

According to a further feature of the invention there is provided a process for the manufacture of the alkanolamine derivative of the invention which comprises assembling in sequence, by chemical synthesis, the five radicals:

i. an aryloxy radical of the formula:

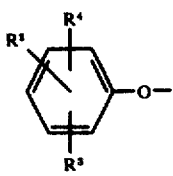

wherein $R^2$, $R^3$ and $R^4$ have the meanings stated above;
 ii. an oxygenated three carbon radical of the formula:

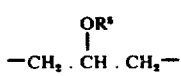

wherein $R^5$ stands for hydrogen or for a protecting group;
 iii. an imino radical of the formula $-NR^6-$, wherein $R^6$ stands for hydrogen or for a protecting group;
 iv. a radical of the formula:

wherein A has the meaning stated above and wherein $R^7$ stands for hydrogen or for a protecting group; and v. a radical of the formula:

wherein $R^1$, X and Y have the meanings stated above; whereafter if one or more of $R^5$, $R^6$ and $R^7$ stands for a protecting group, the one or more protecting groups are removed.

The various stages of the assembly may be carried out in any possible order. Thus, for example:
 a. a phenol of the formula:

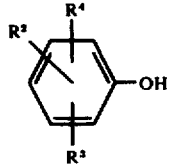

wherein $R^2$, $R^3$ and $R^4$ have the meanings stated above, may first be reacted with an oxygenated three-carbon derivative, for example a compound of the formula:

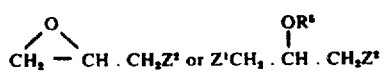

wherein $R^5$ has the meaning stated above, wherein $Z^1$ stands for a displaceable radical and wherein $Z^2$ stands for the hydroxy radical or for a displaceable radical. If $Z^2$ stands for the hydroxy radical, the intermediate compound obtained is further reacted with a reagent which will replace the primary hydroxy radical $Z^2$ with a displaceable radical $Z^1$. The resulting product, which is a compound of the formula:

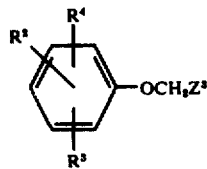

wherein $R^2$, $R^3$ and $R^4$ have the meanings stated above and wherein $Z^3$ stands for the group

or the group $$-\underset{\underset{\displaystyle OR^5}{|}}{CH} . CH_2Z^1,$$

wherein $R^5$ and $Z^1$ have the meanings stated above, or which may be, when $R^5$ stands for hydrogen, a mixture of such compounds wherein $Z^3$ has both meanings stated above, is then reacted with an amine of the formula:

$$HNR^6-A-NR^7-X-Y-R^1$$

wherein A, $R^1$, $R^6$, $R^7$, X and Y have the meanings stated above, or with a precursor of such an amine.

b. An oxygenated three-carbon derivative, for example a compound of the formula:

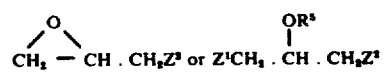

wherein $R^5$, $Z^1$ and $Z^2$ have the meanings stated above, is reacted with an amine of the formula:

$$HNR^6-A-NR^7-X-Y-R^1$$

wherein A, $R^1$, $R^6$, $R^7$, X and Y have the meanings stated above, or with a precursor of such an amine. If $Z^2$ stands for the hydroxy radical the intermediate compound obtained is further reacted with a reagent which will replace the primary hydroxy radical $Z^2$ with a displaceable radical $Z^1$. The resulting product, which is a compound of the formula:

wherein A, $R^1$, $R^6$, $R^7$, X, Y and $Z^3$ have the meanings stated above, or which may be, when $R^5$ stands for hydrogen, a mixture of such compounds wherein $Z^3$ has both meanings stated above, is then reacted with a phenol of the formula:

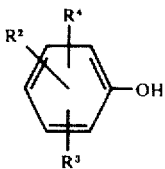

wherein $R^2$, $R^3$ and $R^4$ have the meanings stated above. Alternatively, the compound of the formula:

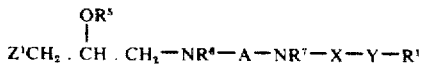

may be converted, by heating, into the azetidinol derivative of the formula:

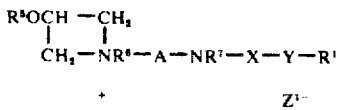

When $R^6$ stands for hydrogen, the azetidinol salt is converted into its free base form and then reacted with a phenol of the formula stated above. When $R^6$ stands for a protecting group, the azetidinium salt is reacted directly with said phenol. The azetidinol derivative may alternatively be obtained by the reaction of a compound of the formula:

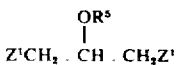

wherein $R^5$ and $Z^1$ have the meanings stated above, with an amine of the formula:

$$HNR^6-A-NR^7-X-Y-R^1$$

wherein A, $R^1$, $R^6$, $R^7$, X and Y have the meanings stated above.

A suitable value for $Z^1$, or for $Z^2$ when it stands for a displaceable radical, is, for example, a halogen atom, for example the chlorine or bromine atom, or a sulphonyloxy radical, for example an alkanesulphonyloxy radical of up to 6 carbon atoms or an arenesulphonyloxy radical of up to 10 carbon atoms, for example the methanesulphonyloxy, benzenesulphonyloxy or toluene-p-sulphonyloxy radical.

A suitable reagent which will replace the primary hydroxy radical $Z^2$ with a displaceable radical $Z^1$ is, for example, a halogenating agent, for example a thionyl halide, for example thionyl chloride or thionyl bromide, or a sulphonylating agent, for example an alkanesulphonyl halide or an arenesulphonyl halide, for example methanesulphonyl chloride, benzenesulphonyl chloride or toluene-p-sulphonyl chloride.

The reaction involving a phenol reactant may be carried out in the presence of an acid-binding agent, for example an alkali metal hydroxide, for example sodium hydroxide, or an organic base, for example piperidine. Alternatively, an alkali metal derivative of the phenol reactant, for example the sodium or potassium derivative, may be used as starting material. The reaction may be carried out in a diluent or solvent, for example methanol or ethanol, and it may be accelerated or completed by the application of heat, for example by heating to the boiling point of the diluent or solvent.

The reaction involving an amine of the formula:

may be carried out at ambient temperature or it may be accelerated or completed by the application of heat, for example by heating to a temperature of 90°–110° C.; it may be carried out at atmospheric or at an elevated pressure, for example by heating in a sealed vessel; and it may be carried out in an inert diluent or solvent, for example methanol, ethanol or n-propanol, or an excess of the amine may be used as diluent or solvent.

c. The series of reactions described under (a) or (b) above may be carried out except that an amine of the formula $R^6NH_2$ is used in place of an amine of the formula:

$$HNR^6-A-NR^7-X-Y-R^1$$

it being understood that when $R^6$ stands for hydrogen the amine is ammonia. The radical $$-A-NR^7-X-Y-R^1$$

may then be inserted as a separate step, for example either by the reaction of the final product from the series of reactions described under (a) or (b) above with a compound of the formula:

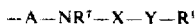

wherein A, $R^1$, $R^7$, X, Y and $Z^1$ have the meanings stated above, or, when $R^6$ stands for hydrogen, by the reaction under reducing conditions of the final product from the series of reactions described under (a) or (b) above with a carbonyl compound of the formula:

$$A^1-CO-A^2-NR^7-X-Y-R^1$$

wherein $R^1$, $R^7$, X and Y have the meanings stated above and wherein $A^1$ stands for hydrogen or for an alkyl radical and $A^2$ stands for an alkylene radical such that the radical

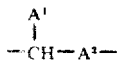

has the same meaning as is stated above for A.

The reaction involving a compound of the formula:

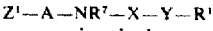

may conveniently be carried out in the presence of a base, for example sodium or potassium carbonate, in a diluent or solvent, for example ethanol or isopropanol, at an elevated temperature, for example at the boiling point of the diluent or solvent.

Suitable reducing conditions for the reaction involving the carbonyl compound are those provided by the presence of hydrogen and a hydrogenation catalyst, for example palladium or platinum, in an inert diluent or solvent, for example in one or more solvents selected from water, ethanol and an excess of the carbonyl compound used as starting materials; or by the presence of an alkali metal borohydride, for example sodium borohydride or lithium cyanoborohydride, in an inert diluent or solvent, for example in one or more solvents selected from water, ethanol, methanol and an excess of the carbonyl compound used as starting material. It is to be understood that when in the starting material $R^1$ stands for an alkenyl radical, or one or more of $R^2$, $R^3$, $R^4$, $R^{12}$ and $R^{13}$ stands for a halogen atom or for a nitro, cyano, alkenyl, alkynyl, alkoxy, alkenyloxy, alkynyloxy or α-aralkoxy radical, hydrogen and a hydrogenation catalyst are preferably not used to provide the reducing conditions, in order to prevent the radical $R^1$, $R^2$, $R^3$, $R^4$, $R^{12}$ or $R^{13}$ from being affected by catalytic hydrogenation.

d. The series of reactions described under (a) or (b) above may be carried out except that an amine of the formula:

wherein $R^6$, $R^7$ and A have the meanings stated above, is used in place of an amine of the formula:

or the reaction described under (c) above may be carried out except that the radical —A—$NHR^7$ is inserted in place of the radical —A—$NR^7$—X—Y—$R^1$. The amidic linkage —$NR^7$—X— may then be formed as a separate step by reaction of the resulting product, which is a compound of the formula:

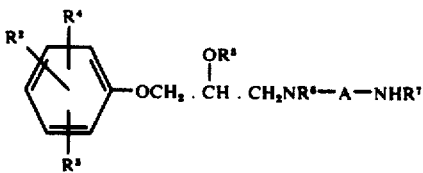

wherein $R^2$, $R^3$, $R^4$, $R^5$, $R^6$, $R^7$ and A have the meanings stated above, with a compound of the formula:

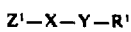

wherein $R^1$, X, Y and $Z^1$ have the meanings stated above, or, when X stands for the carbonyl radical and Y stands for the imino radical, with an isocyanate of the formula:

wherein $R^1$ has the meaning stated above.

e. A compound wherein one or more of $R^5$, $R^6$ and $R^7$ stands for a protecting group may be prepared by the series of reactions described under (a) or (b) or (c) or (d) above. Alternatively, a suitable protecting group may be introduced by conventional means into an intermediate compound at any stage preceding the final stage.

A suitable value for $R^5$ when it stands for a protecting group is, for example, a hydrogenolysable radical, for example an α-arylalkyl, α-arylalkoxy-carbonyl or α-arylalkoxymethyl radical, for example the benzyl, benzyloxycarbonyl or benzyloxymethyl radical, or an acyl radical, for example an alkanoyl radical of up to 20 carbon atoms, for example the acetyl, t-butoxycarbonyl or 2,2,2-trichloroethoxycarbonyl radical, or an aroyl radical of up to 10 carbon atoms, for example the benzoyl radical, or an α-alkoxyalkyl radical (that is, a radical which forms with the oxygenated three-carbon radical an acetal radical), for example the tetrahydropyranyl radical, or a tertiary alkyl radical, for example the t-butyl radical.

A suitable value for $R^6$ when it stands for a protecting group is, for example, a hydrogenolysable or tertiary alkyl radical as defined for $R^5$, or a relatively easily hydrolysable acyl radical, for example the 2,2,2-trichloroethoxycarbonyl or t-butoxycarbonyl radical. It is to be understood that when $R^6$ stands for an acyl radical, this radical must be removable under conditions which will not destroy the amidic linkage —$NR^7$—X.

Alternatively, $R^5$ and $R^6$ may be joined together so that one protecting group serves to protect both the oxygen and nitrogen atoms. Such a protecting group may be, for example, a radical of the formula —CH$R^8$—, wherein $R^8$ stands for hydrogen, or for an alkyl radical of up to 4 carbon atoms or an aryl radical of up to 10 carbon atoms, such that it forms, together with the adjacent oxygen and nitrogen atoms and two carbon atoms of the three-carbon radical, an oxazolidine nucleus.

A suitable value for $R^7$ when it stands for a protecting groups is, for example, a hydrogenolysable or tertiary alkyl group as defined for $R^5$ or $R^6$.

The hydrogenolysable protecting group $R^5$, $R^6$ or $R^7$ may be removed, for example, by catalytic hydrogenolysis, for example by hydrogenation in the presence of a palladium-on-charcoal catalyst, in an inert diluent or solvent, for example ethanol or aqueous ethanol. The process may be accelerated or completed by the presence of an acidic catalyst, for example hydrochloric or oxalic acid.

The acyl protecting group $R^5$ or $R^6$ may be removed by hydrolysis in the presence of a base, for example an alkali metal hydroxide, in a diluent or solvent, for example water, methanol, or ethanol or a mixture thereof. It is to be understood that the hydrolytic conditions used must be sufficiently mild to avoid hydrolysis of the amidic linkage —$NR^7$—X.

The α-alkoxyalkyl protecting group $R^5$ or the protecting group —$R^8$CH—formed by $R^5$ and $R^6$ taken together may be removed by hydrolysis in the presence of an acid, for example a mineral acid, for example aqueous hydrochloric acid, and the hydrolysis may be carried out at a temperature of up to 100° C.

The tertiary alkyl protecting group $R^5$, $R^6$ or $R^7$, or the acyl protecting group $R^5$ or $R^6$ when it stands for a tertiary alkoxycarbonyl radical, for example the t-butoxycarbonyl radical, may be removed by treatment with an acid, for example hydrogen chloride, in anhydrous conditions, for example in ethereal solution.

A compound wherein one or more of $R^2$, $R^3$, $R^4$, $R^{12}$ and $R^{13}$ stands for an α-arylalkoxy radical, for example the benzyloxy radical, may be converted into the corresponding compound wherein one or more of $R^2$, $R^3$, $R^4$, $R^{12}$ and $R^{13}$ stands for the hydroxy radical by hydrogenolysis.

A preferred process for the manufacture of the alkanolamine derivative of the invention comprises the reaction of a compound of the formula:

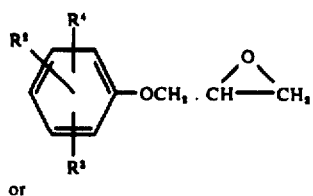

or

-continued

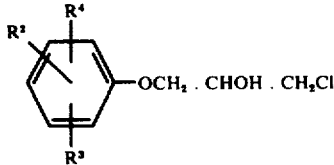

wherein $R^2$, $R^3$ and $R^4$ have the meanings stated above (both of which compounds may be obtained by the reaction of the corresponding phenol with epichlorohydrin), with an amine of the formula:

$$R^6NH-A-NH-X-Y-R^1$$

wherein A, $R^1$, X and Y have the meanings stated above and wherein $R^6$ stands for hydrogen or for the benzyl radical, whereafter if $R^6$ stands for the benzyl radical this radical is removed by hydrogenolysis.

Optically-active enantiomorphs of the alkanolamine derivative of the invention may be obtained by the resolution by conventional means of the corresponding racemic alkanolamine derivative of the invention.

The said resolution may be carried out by reacting the racemic alkanolamine derivative with an optically-active acid, followed by fractional crystallisation of the diastereoisomeric mixture of salts thus obtained from a diluent or solvent, for example ethanol, whereafter the optically-active alkanolamine derivative is liberated from the salt by treatment with a base. A suitable optically-active acid is, for example, (+)- or (−)-O,O-di-p-toluoyltartaric acid or (−) -2,3:4,5-di-O-isopropylidene-2-keto-L-gulonic acid.

The resolution process may be facilitated by treating the partially resolved alkanolamine derivative in free base form obtained after a single fractional crystallisation of the diasteroisomeric mixture of salts wth a solubilising agent, for example a primary amine, for example Ilylamine, in a relatively non-popular diluent or solvent, for example petroleum ether.

The alkanolamine derivative of the invention in free base form may be converted into an acid-addition salt thereof by reaction with an acid by conventional means.

As stated above, the alkanolamine derivative of the invention or an acid-addition salt thereof possesses β-adrenergic blocking activity, and furthermore this activity is cardioselective. This activity may be determined by the reversal of isoprenaline-induced tachycardia in rats or cats, a standard test for the determination of β-adrenergic blocking activity, and by relative freedom form antagonism of isoprenaline-induced vasodilation in cats or of the relief produced by isoprenaline of histamine-induced bronchospasm in guinea-pigs. Compounds exhibiting this cardioselective action show a greater degree of specificity in blocking the cardiac β-receptors than the β-receptors in peripheral blood vessels and bronchial muscle. Thus, a dose may be selected for such a compound at which the compound blocks the cardiac inotropic and chronotropic actions of a catecholamine such as isoprenaline but does not block the relaxation of tracheal smooth muscle produced by isoprenaline or the peripheral vasodilator action of isoprenaline. Because of this selective action, one of these compounds may advantageously be used together with a sympathominetic bronchodilator, for example isoprenaline, orciprenaline, adrenaline or ephedrine, in the treatment of asthma and other obstructive airways diseases, inasmuch as the cardioselective compound will substantially inhibit the unwanted stimulatory effects of the bronchodilator on the heart but will not hinder the desirable therapeutic effect of the bronchodilator. A preferred alkanolamine derivative of the invention is three to ten times more active as a cardioselective β-adrenergic blocking agent than practolol. At doses of an alkanolamine derivative of the invention which produce effective β-adrenergic blockade in rats or cats, no symptoms of toxicity are apparent.

Some of the alkanolamine derivatives of the invention wherein one or more of the substituents $R^2$, $R^3$ and $R^4$ stands for the hydroxy radical, and in particular those wherein $R^4$ stands for a hydroxy radical in the 3- or 4-position of the benzene nucleus, $R^2$ stands for the hydrogen atom or for a hydroxy radical in the 3-position when $R^4$ is in the 4-position of the benzene nucleus and $R^3$ stands for the hydrogen atom possess, in addition to β-adrenergic blocking activity, substantial cardiac stimulant activity. This may be demonstrated in either conscious or pentobarbitone-anaesthetised dogs, where the alkanolamine derivative or salt thereof produces an increase in heart rate, and/or an increase in force of contraction of the heart and an increase in the speed of conduction of electrical activity through the tissues of the heart. Unlike isoprenaline, a known cardiac stimulating agent, a preferred stimulant alkanolamine derivative of the invention or a salt thereof is well absorbed when administered orally and has a substantial duration of action. At doses of an alkanolamine derivative of the invention which produce effective cardiac stimulation in dogs, no symptoms of toxicity are apparent.

The alkanolamine derivative of the invention may be administered to warm-blooded animals, including man, in the form of a pharmaceutical composition comprising as active ingredient at least one alkanolamine derivative of the invention, or an acid-addition salt thereof, in association with a pharmaceutically-acceptable diluent or carrier therefor.

A suitable composition is, for example, a tablet, capsule, aqueous or oil solution or suspension, emulsion, injectable aqueous or oil solution or suspension, dispersible powder, spray or aerosol formulation.

The pharmaceutical composition may contain, in addition to the alkanolamine derivative of the invention, one or more drugs selected from sedatives, for example phenobarbitone, meprobamate, chlorpromazine and the benzodiazepine sedative drugs, for example chlordiazepoxide and diazepam; vasodilators, for example glyceryl trinitrate, pentaerythritol tetranitrate and isosorbide dinitrate; diuretics, for example chlorothiazide; hypotensive agents, for example reserpine, bethanidine and guanethidine; cardiac membrane stabilising agents, for example quinidine; agents used in the treatment of Parkinson's disease and other tremors, for example benzhexol; cardiotonic agents, for example digitalis preparations; α-adrenergic blocking agents, for example phentolamine and sympathomimetic bronchodilators, for example isoprenaline, orciprenaline, adrenaline and ephedrine.

When used for the treatment of heart diseases, for example angina pectoris and cardiac arrhythmias, or for the treatment of hypertension or anxiety states in man, it is expected that the alkanolamine derivative would be given to man at a total oral dose of between 20 mg. and 600 mg. daily, at doses spaced at 6–8 hourly intervals, or at an intravenous dose of between 1 mg. and 20 mg.

When used for the treatment of acute or chronic heart failure in man, it is expected that a cardiac stimulant alkanolamine derivative would be given to man at a total oral dose of between 10 mg. and 200 mg. daily, at doses spaced at 6–8 hourly intervals, or at an intravenous dose of between 1 mg. and 100 mg.

Preferred oral dosage forms are tablets or capsules containing between 10 and 100 mg., and preferably 10 mg. or 50 mg. of active ingredient. Preferred intravenous dosage forms are sterile aqueous solutions of the alkanolamine derivative or of a non-toxic acid-addition salt thereof, containing between 0.05% and 1% w/v of active ingredient, and more particularly containing 0.1% w/v of active ingredient.

The invention is illustrated but not limited by the following Examples:

EXAMPLE 1

A mixture of 3.0 g. of 2, 3-epoxy-1-phenoxypropane, 50 ml. of n-propanol, 4.0 g. of β-benzamidoethylamine hydrochloride and a solution of 0.8 g. of sodium hydroxide in 5 ml. of water is heated under reflux for 18 hours. The mixture is evaporated to dryness under reduced pressure and the residue is stirred with 40 ml. of aqueous 2N-hydrochloric acid. The mixture is filtered and the solid residue is crystallised from ethanol. There is thus obtained 3-β-benzamidoethylamino-1-phenoxy-2-propanol hydrochloride, m.p. 198°–199° C.

EXAMPLE 2

A mixture of 0.75 g. of 2,3-epoxy-1-phenoxypropane, 25 ml. of n-propanol, 1.18 g. of β-benzenesulphonamidoethylamine hydrochloride and a solution of 0.42 g. of sodium bicarbonate in 5 ml. of water is heated under reflux for 18 hours. The mixture is evaporated to dryness under reduced pressure and the residue is stirred with 25 ml. of aqueous N-sodium hydroxide solution. The mixture is washed three times with 25 ml. of ether each time, and the aqueous alkaline phase is neutralised with glacial acetic acid. The mixture is extracted three times with 25 ml. of ethyl acetate each time, and the combined extracts are dried over anhydrous magnesium sulphate and filtered. The filtrate is added to a solution of 0.6 g. of oxalic acid in 30 ml. of ethyl acetate. The mixture is filtered and the solid residue is washed with ethyl acetate and recrystallised from acetonitrile. There is thus obtained 1-phenoxy-3-β-benzenesulphonamidoethylamino-2-propanol oxalate, m.p. 135°–137° C.

EXAMPLE 3

A mixture of 1.5 g. of 2,3 -epoxy-1-phenoxypropane, 50 ml. of n-propanol, 2.31 g of β-phenoxyacetamidoethylamine hydrochloride and a solution of 0.4 g. of sodium hydroxide in 5 ml. of water is heated under reflux for 18 hours. The mixture is evaporated to dryness under reduced pressure and the residue is stirred with 20 ml. of aqueous N-sodium hydroxide solution. The mixture is extracted three times with 20 ml. of ethyl acetate each time, and the combined extracts are dried over anhydrous magnesium sulphate and filtered. The filtrate is added to a solution of 2.5 g. of oxalic acid in 100 ml. of ether. The mixture is filtered and the solid residue is crystallised from acetonitrile. There is thus obtained 1-phenoxy-3-β-phenoxyacetamidoethylamino-2-propanol oxalate, m.p. 131°–133° C.

The β-phenoxyacetamidoethylamine hydrochloride used as starting material may be obtained as follows:

A mixture of 8.3 g. of methyl phenoxyacetate and 10.8 ml. of ethylenediamine is heated at 90° C. for 18 hours and then cooled and stirred with 70 ml. water. The mixture is filtered and the filtrate is evaporated to dryness under reduced pressure. The residue is dissolved in ethyl acetate, dried over anhydrous magnesium sulphate and filtered, and the filtrate is acidified with ethereal hydrochloric acid. The mixture is filtered and the solid residue is crystallised from ethanol. There is thus obtained β-phenoxyacetamidoethylamine hydrochloride, m.p. 159°–160° C.

EXAMPLE 4

A mixture of 1.5 g. of 2,3-epoxy-1-phenoxypropane, 50 ml. of n-propanol, 2.15 g. of β-phenylacetamidoethylamine hydrochloride and a solution of 0.4 g. of sodium hydroxide in 5 ml. of water is heated under reflux for 18 hours. The mixture is evaporated to dryness under reduced pressure and the residue is stirred with 20 ml. of aqueous N-sodium hydroxide solution. The mixture is extracted three times with 20 ml. of ethyl acetate each time and the combined extracts are dried over anhydrous magnesium sulphate and filtered. The filtrate is evaporated to dryness under reduced pressure and the residue is crystallised from ethyl acetate. There is thus obtained 1-phenoxy-3-β-phenylacetamidoethylamino-2-propanol, m.p. 124°–125° C.

EXAMPLE 5

A mixture of 1.5 g. of 2,3-epoxy-1-phenoxypropane, 50 ml. of n-propanol and 1.79 g. of β-(3-phenylureido)ethylamine is heated under reflux for 18 hours. The mixture is evaporated to dryness under reduced pressure and the residue is crystallised from ethyl acetate. There is thus obtained 1-phenoxy-3-β-(3-phenylureido)ethylamino-2-propanol, m.p. 144°–145° C.

EXAMPLE 6

The process described in Example 1 is repeated except that the appropriate 2,3-epoxy-1-phenoxypropane (or the corresponding 3-chloro-1-phenoxy-2-propanol) and the appropriate β-carboxamidoethylamine are used as starting materials. There are thus obtained the compounds described in the following table :

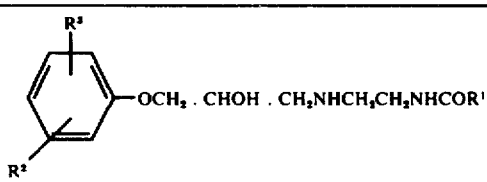

-continued

| R¹ | R² | R³ | m.p. (° C.) | Crystallisation solvent |
|---|---|---|---|---|
| methyl | H | H | 103–105 | ethyl acetate |
| ethyl | H | H | 126–127 | acetonitrile |
| n-propyl | H | H | 86–87 | ethyl acetate |
| isopropyl | H | H | 125–126 | ethyl acetate |
| n-octyl | H | H | 95–96 | ethyl acetate |
| cyclopropyl | H | H | 125–126 | ethyl acetate |
| cyclopentyl | H | H | 133–135 | ethyl acetate |
| cyclohexyl | H | H | 138–139 | acetonitrile |
| 2-chloro-phenyl | H | H | hydrochloride 182–183 | acetonitrile |
| 4-tolyl | H | H | hydrochloride 211–212 | acetonitrile |
| 2-nitro-phenyl | H | H | 131–132 | ethyl acetate/ petroleum ether |
| 2-methoxy-phenyl | H | H | hydrogen oxalate 164–165 | ethanol |
| 2-dimethyl-aminophenyl | H | H | 82–84 | ethyl acetate |
| isopropyl | 2-cyano | H | 109–110 | ethyl acetate |
| isopropyl | 2-nitro | H | 108–110 | ethyl acetate |
| isobutyl | H | H | 114–115 hydrogen oxalate | ethyl acetate |
| t-butyl | H | H | 167–168 | ethanol |
| n-pentyl | H | H | 101–102 | ethyl acetate |
| ethyl | 2-cyano | H | 96–97 | ethyl acetate/ petroleum ether |
| isopropyl | 2-chloro | H | 129–130 | ethyl acetate |
| isopropyl | 2-methyl | H | 120–122 | ethyl acetate |
| isopropyl | 2-methoxy | H | 142–143 | acetonitrile |
| isopropyl | 2-chloro | 4-methyl | 119–120 | ethyl acetate |
| isopropyl | 2-chloro | 5-chloro | 152–153 | acetonitrile |
| isopropyl | 2-nitro | 4-methoxy | 122–124 | ethyl acetate |
| methyl | 3-cyano | H | 121–122 | ethyl acetate |
| 4-benzyloxy-phenyl | H | H | 124–126 | acetonitrile |
| isopropyl | 2-benzyloxy | H | 137–138 | acetonitrile |
| 3,4-dibenzyloxy-phenyl | H | H | hydrochloride 223–224 | ethanol |

Many of the β-carboxamidoethylamines used as starting materials are novel compounds, and may be prepared by a process exemplified by the following preparation of β-cyclopentane-carboxamidoethylamine:

A mixture of 12.8 g. of methane cyclopentanecarboxylate and 26.6 ml. of ethylenediamine is heated at 90° C. for 18 hours and then cooled and stirred with 100 ml. of water. The mixture is filtered and the filtrate is evaporated to dryness under reduced pressure. The residue is extracted with 50 ml. of toluene and the extract is evaporated to dryness under reduced pressure. The residue is then dissolved in 200 ml. of ethyl acetate and the solution is added to a solution of 2.4 g. of oxalic acid in a mixture of 250 ml. of acetone and 250 ml. of ethyl acetate. The mixture is filtered and the solid residue is crystallised from ethanol. There is thus obtained β-cyclopentanecarboxamidoethylamine hydrogen oxalate, m.p. 164°–165° C.

The following amines may similarly be prepared from the appropriate methyl or ethyl ester and ethylenediamine:

R¹—CONH—CH₂CH₂NH₂

| R¹ | Salt | m.p. (° C.) | Crystallisation solvent |
|---|---|---|---|
| n-octyl | hydrochloride | 217–221 | ethanol |
| cyclopropyl | hydrogen oxalate | 147–149 | ethanol |
| cyclohexyl | hydrogen oxalate | 154–155 | ethanol/ethyl acetate |
| 2-chlorophenyl | hydrochloride | 164–166 | ethanol/ethyl acetate |
| 2-methoxy-phenyl | hydrogen oxalate | 163–164 | ethanol |
| 2-dimethylamino-phenyl | dihydro-chloride | 220–221 | ethanol |
| ethyl | hydrogen oxalate | 133–134 | ethanol |
| n-propyl | hydrogen oxalate | 120–121 | ethanol/ethyl acetate |
| isopropyl | hydrogen oxalate | 130–131 | ethanol |
| isobutyl | hydrogen oxalate | 100–102 | ethanol/ethyl acetate |
| t-butyl | hydrogen oxalate | 188–189 (with decomposition) | ethanol |
| n-pentyl | (free base) | b.p.142° C./ 0.2 mm. | — |
| 4-benzyloxy-phenyl | (free base) | 118–120 | toluene |
| 3,4-dibenzyl-oxyphenyl | (free base) | 128–130 | ethanol |

EXAMPLE 7

The process described in Example 2 is repeated except that the appropriate 2,3-epoxy-1-phenoxypropane and the appropriate β-sulphonamidoethylamine are used as starting materials. There are thus obtained the compounds described in the following table:

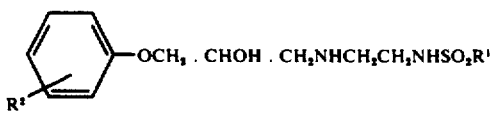

| R¹ | R² | m.p. (° C.) | Crystallisation solvent |
|---|---|---|---|
| methyl | H | 155–156 | methanol |
| 4-tolyl | H | 145–148 | ethanol |
| 4-chlorophenyl | H | 166–169 | ethanol |
| 2-nitrophenyl | H | 186–188 | acetonitrile |
| 3-nitrophenyl | H | 166–167 | methanol |
| isopropyl | H | oxalate 181–183 | ethanol |
| n-propyl | H | 87–88 | ethyl-acetate/ petroleum ether |
| phenyl | 2-cyano | hydrogen oxalate monohydrate 136–138 (with decomposition) | ethanol |
| 4-aminophenyl | H | oxalate 158–160 (with decomposition) | ethanol |
| 3-amino-4-methyl-5-nitrophenol | H | hemioxalate 223–225 (with decomposition) | ethyl acetate |

The β-methanesulphonamidoethylamine used as starting material may be obtained as follows:

Methanesulphonyl chloride (5.7 g.) is added dropwise during 10 minutes to a cooled solution of 30 g. of ethylenediamine in 100 ml. of water and the mixture is stirred for a further 30 minutes and then neutralised with 4.2 g. of sodium bicarbonate. The mixture is evaporated to dryness under reduced pressure and the residue is extracted three times with 200 ml. of boiling acetonitrile each time. The combined extracts are dried over anhydrous magnesium sulphate and evaporated to dryness under reduced pressure and the residue is dissolved in a mixture of 90 ml. of ethyl acetate and 10 ml. of methanol. The solution is added to a solution of 6 g. of oxalic acid in 100 ml. of ethyl acetate, the mixture is filtered and the solid residue is washed with ethyl acetate. There is thus obtained 2-methanesulphonamidoethylamine hydrogen oxalate, m.p. 170°–174° C. (with decomposition).

Other novel β-sulphonamidoethylamines which may similarly be prepared and which have been characterised are described in the following table:

R¹—SO₂NH—CH₂CH₂NH₂

| R¹ | Salt | m.p. (° C.) | Crystallisation solvent |
|---|---|---|---|
| isopropyl | hydrogen oxalate | 166–167 | ethanol |
| n-propyl | hydrogen oxalate hemihydrate | 145–147 | ethanol |
| 3-amino-4-methyl-5-nitrophenyl | hydrochloride | 222–225 | ethanol |

EXAMPLE 8

The process described in Example 4 is repeated except that the appropriate 2,3-epoxy-1-phenoxypropane and the appropriate β-carboxamidoethylamine are used as starting materials. There are thus obtained the compounds described in the following table:

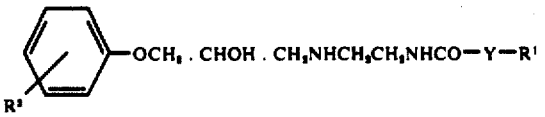

| R¹ | Y | R² | m.p. (° C.) | Crystallisation solvent |
|---|---|---|---|---|
| 4-chlorophenyl | —CH₂— | H | 119–120 | acetonitrile |
| 2-chlorophenyl | —CH₂— | H | 137–138 | ethyl acetate |
| phenyl | —CH₂CH₂— | H | 112–113 | ethyl acetate/ petroleum ether |
| 4-chlorophenyl | —CH₂O— | H | 163–164 | methanol |
| phenyl | —CH₂CH₂CH₂O— | H | 89–91 | ethyl acetate/ petroleum ether |
| ethyl | —O— | H | 87–88 | ethyl acetate/ petroleum ether |
| H | —CH₂O— | H | hydrogen oxalate 128–129 | ethanol |
| methyl | —CH₂O— | H | hydrogen oxalate 135–137 (with decomposition) | ethanol |
| 2-nitrophenyl | —CH₂— | H | 130–131 | ethyl acetate |
| 4-nitrophenyl | —CH₂— | H | 135–136 | ethyl acetate |
| 4-methoxyphenyl | —CH₂— | H | 122–123 | ethyl acetate |
| 2-chlorophenyl | —CH₂— | 2-cyano | 120–122 | acetonitrile |
| 2-chlorophenyl | —CH₂— | 2-chloro | 144–146 | ethyl acetate |
| 4-chlorophenyl | —C(CH₃)₂O— | H | hydrogen oxalate 172–174 | ethanol |

-continued

| | | | | |
|---|---|---|---|---|
| 2-methoxy-phenyl | —CH$_2$O— | H | hydrogen oxalate 156–158 | acetonitrile |

The β-carboxamidoethylamines used as starting material may be prepared by a similar process to that described in the second part of Example 6. Those amines which have been characterised are described in the following table:

| | R$^1$—Y—CONHCH$_2$CH$_2$NH$_2$ | | | |
|---|---|---|---|---|
| R$^1$—Y— | Salt | m.p. (° C.) | | Crystallisation solvent |
| 4-chlorophenyl—CH$_2$— | hydrochloride | 194–196 | | ethanol/ ethyl acetate |
| 2-chlorophenyl—CH$_2$— | hydrochloride | 162–163 | | ethanol/ ethyl acetate |
| phenyl—CH$_2$CH$_2$— | hydrochloride | 134–137 | | ethanol/ ethyl acetate |
| 4-chlorophenyl—OCH$_2$— | p-chlorophenoxy-acetate | 147–148 | | acetonitrile |
| phenyl—OCH$_2$CH$_2$CH$_2$— | hydrochloride | 137–140 | | acetonitrile |
| methyl—OCH$_2$— | hydrogen oxalate | 137–138 | | ethanol |
| 4-methoxyphenyl-CH$_2$— | (free base) | 130–140 | | toluene |
| 4-chlorophenyl-OC(CH$_3$)$_2$— | hydrochloride | 98–100 | | acetonitrile |

The β-hydroxyacetamidoethylamine used as starting material may be obtained by heating 2-hydroxymethylimidazoline (m.p. 87°–88° C., obtained from ethyl glycollate and ethylenediamine), under reflux with water for 15 minutes.

EXAMPLE 9

The process described in Example 5 is repeated except that the appropriate 2,3-epoxy-1-phenoxypropane and the appropriate β-ureidoethylamine are used as starting materials. There are thus obtained the compounds described in the following table:

| R$^1$ | R$^2$ | m.p. (° C.) | Crystallisation solvent |
|---|---|---|---|
| ethyl | H | 118–120 | ethyl acetate |
| isopropyl | H | 145–147 | acetonitrile |
| n-butyl | H | 116–117 | ethyl acetate |
| allyl | H | 131–132 | ethyl acetate |
| 4-tolyl | H | 147–149 | ethyl acetate |
| 4-methoxyphenyl | H | 126–128 | ethyl acetate |
| phenyl | 2-chloro | 157–158 | acetonitrile |
| phenyl | 2-nitro | 159–161 | acetonitrile |
| phenyl | 2-methyl | 160–161 | acetonitrile |
| phenyl | 2-cyano | 155–156 | acetonitrile |
| n-butyl | 2-chloro | 149–150 | acetonitrile |
| n-butyl | 2-methyl | 136–137 | acetonitrile |
| n-butyl | 2-cyano | 145–147 | acetonitrile |

The β-(3-n-butylureido)ethylamine used as starting material may be obtained as follows:

A solution of 22.6 ml. of n-butyl isocyanate in 50 ml. of chloroform is added dropwise during 45 minutes to a solution of 26.6 ml. of ethylenediamine in 50ml. of chloroform which is cooled to between −10° C. and 0° C. The mixture is then stirred at laboratory temperature for 2 hours and filtered, and the filtrate is evaporated to dryness under reduced pressure. The residue is dissolved in 150 ml. of toluene and the mixture is evaporated to dryness. The residue is dissolved in 50 ml. of ethyl acetate and the solution is added to a solution of 12.4 g. of oxalic acid in 100 ml. of ethyl acetate. The ethyl acetate is removed by decantation and the residue is triturated with 50 ml. of acetonitrile. The mixture is filtered and the solid residue is crystallised from ethanol. There is thus obtained β-(3-n-butylureido)-ethylamine hydrogen oxalate, m.p. 138°–139° C.

Other novel β-ureidoethylamines which may similarly be prepared and which have been characterised are described in the following table:

| | R$^1$—NHCONH—CH$_2$CH$_2$NH$_2$ | | |
|---|---|---|---|
| R$^1$ | Salt | m.p. (° C) | Crystallisation solvent |
| ethyl | hydrochloride | 122–124 | isopropanol/ ethyl acetate |
| isopropyl | hydrogen oxalate | 146–148 | ethanol/ acetonitrile |
| allyl | hydrochloride | 128–130 | isopropanol |
| 4-tolyl | hydrochloride | 234–236 | ethyl acetate |
| 4-methoxy-phenyl | (free base) | 104–106 | ethyl acetate |

EXAMPLE 10

The process described in Example 5 is repeated except that the appropriate 2,3-epoxy-1-phenoxypropane and the appropriate β-carboxamidoalkylamine are used as starting materials. There are thus obtained the compounds described in the following table:

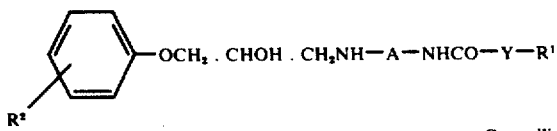

| R¹ | Y | A | R² | m.p. (° C) | Crystallisation solvent |
| --- | --- | --- | --- | --- | --- |
| isopropyl | direct | —(CH₂)₄— | H | hydrogen oxalate 128–130 | acetonitrile |
| methyl | direct | —(CH₂)₆— | H | hydrogen oxalate 111–113 | acetonitrile |
| phenyl | —CH₂— | —CHCH₂— \| CH₃ | H | 124–126 | ethyl acetate |
| phenyl | —CH₂— | —CHCH₂— \| CH₃ | 2-cyano | 124–128 | ethyl acetate |
| isopropyl | direct | —CHCH₂— \| CH₃ | H | 124–126 | ethyl acetate |
| n-pentyl | direct | —CHCH₂— \| CH₃ | H | 102–103 | ethyl acetate |
| isopropyl | direct | —(CH₂)₃— | H | 94–95 | ethyl acetate |
| n-pentyl | direct | —(CH₂)₄— | H | 85–86 | ethyl acetate |
| phenyl | —CH₂— | —CHCH₂— \| CH₃ | 2-nitro | 115–117 | ethyl acetate |
| phenyl | —CH₂— | —CHCH₂— \| CH₃ | 2-allyl-oxy | 102–105 | ethyl acetate |

The 1-methyl-2-(phenylacetamido)ethylamine used as starting material may be obtained as follows:

A mixture of 32.8 g. of ethyl phenylacetate and 44.4 g. of 1,2-diaminopropane is heated at 90° C. for 18 hours and then dissolved in 100 ml. of toluene. The solution is evaporated to dryness under reduced pressure, the residue is triturated with 100 ml. of acetonitrile and 200 ml. of ether and the mixture is filtered. The solid residue is crystallised from acetonitrile and then stirred with a mixture of 10 ml. of aqueous 2N-sodium hydroxide solution and 20 ml. of saturated aqueous sodium chloride solution. The mixture is extracted four times with 50 ml. of chloroform each time and the combined extracts are dried over anhydrous magnesium sulphate and evaporated to dryness under reduced pressure. The residue is triturated with ether and petroleum ether (b.p. 60°–80° C.) and the mixture is filtered. The solid residue is washed with petroleum ether (b.p. 60°–80° C.) and there is thus obtained 1-methyl-2-(phenylacetamido)ethylamine, m.p. 46°–48° C.

There may similarly be obtained:
from ethyl isobutyrate and 1,2-diaminopropane, 1-methyl-2-isobutyramidoethylamine, b.p. 106° C./0.3 mm. (hydrogen oxalate m.p. 141°–143° C. after crystallisation from a mixture of ethanol and ethyl acetate);
from ethyl hexanoate and 1,2-diaminopropane, 1-methyl-3-hexanamidoethylamine, b.p. 136° C./0.15 mm.;
from methyl isobutyrate and 1,3-diaminopropane, γ-isobutyramidopropylamine, b.p. 120°–122° C./0.2 mm.;
from ethyl isobutyrate and 1,4-diaminobutane, 4-isobutyramidobutylamine (hydrochloride m.p. 153°–154° C. after crystallisation from a mixture of ethanol and ethyl acetate);
from ethyl acetate and 1,6-diaminohexane, 6-acetamidohexylamine, b.p. 123°–130° C./0.13 mm.

EXAMPLE 11

A mixture of 0.64 g. of 3-benzylamino-1-phenoxy-2-propanol, 1.44 g. of β-(2-methyl-2-p-chlorophenoxybutyramido) ethyl chloride and 0.42 g. of sodium bicarbonate is heated at 120° C. for 18 hours and then cooled and stirred with 25 ml. of ethyl acetate and 25 ml. of water. The ethyl acetate phase is separated, dried over anhydrous magnesium sulphate and evaporated to dryness under reduced pressure. There is thus obtained as an oil, which is used without further purification, 1-phenoxy-3-[N-benzyl-N-β-(2-methyl-2-p-chlorophenoxybutyramido)ethyl] amino-2-propanol.

A mixture of 1.9 g. of the above compound, 40 ml. of ethanol, 1 ml. of 11 N-aqueous hydrochloric acid and 0.2 g. of a 30% palladium-on-charcoal catalyst is shaken with hydrogen at laboratory temperature and atmospheric pressure until the uptake of hydrogen ceases. The mixture is filtered and the filtrate is evaporated to dryness under reduced pressure. The residue is dissolved in 50 ml. of ether and the solution is added to a solution of 0.6 g. of oxalic acid in 25 ml. of ethyl acetate. The mixture is filtered and the solid residue is crystallised from acetonitrile. There is thus obtained 1-phenoxy-3-β-(2-methyl-2-phenoxybutyramido)ethylamino-2-propanol oxalate, m.p. 112°–113° C.

EXAMPLE 12

A solution of 2.5 g. of 1-phenoxy-3-β-(p-benzyloxybenzamido)ethylamino-2-propanol (Example 6) in 50 ml. of a 1:1 v/v mixture of ethanol and acetic acid is shaken for 1 hour with hydrogen at laboratory temperature and atmospheric pressure in the presence of 400 mg. of a 5% palladium-on-charcoal, when 180 ml. of hydrogen have been absorbed. The mixture is filtered, the filtrate is evaporated to dryness under reduced pressure and the residue is dissolved in water. The solution is extracted with ethyl acetate and the extract is dried and evaporated to dryness. The residue is dissolved in ethyl acetate and a solution of oxalic acid in the appropriate β-substituted-ethylamine derivative (prepared as hereinbefore described), and there are thus obtained the compounds described in the following tables:

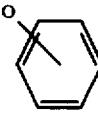

| position of HO— substituent | R¹—Y— | base or salt | m.p. (° C) | Crystallisation solvent |
|---|---|---|---|---|
| 2- | phenyl—NH— | base | 154 | ethanol |
| 4- | ethyl- | hemi-oxalate | 149 | ethanol/ether |
| 4- | methoxy—CH₂— | oxalate | 199 (with decomposition) | ethanol |
| 4- | phenyl- | acetate | 145–146 | ethanol |
| 4- | phenyl—CH₂— | hemi-oxalate hydrate | 110 (with decomposition) | ethanol |
| 3- | isopropyl | base | (oil) | — |
| 2- | isopropyl | hydrogen oxalate | 168–170 | ethanol/acetonitrile |

| position of HO— substitutent | R¹ | base or salt | m.p. (° C) | Crystallisation solvent |
|---|---|---|---|---|
| 4- | phenyl | hemi-oxalate | 158–159 | methanol |
| 3- | phenyl | oxalate hydrate | (glass) | — |
| 4- | methyl | oxalate | 119.5–120 (with decomposition). | ethanol | acetone is added. The mixture is filtered and the solid residue is crystallised from ethanol. There is thus obtained 1-phenoxy-3-β-(p-hydroxybenzamido)ethylamino-2-propanol hydrogen oxalate, m.p. 152°–154° C. (with decomposition).

EXAMPLE 13

A mixture of 2.5 g. of 1-p-benzyloxyphenoxy-2,3-epoxypropane, 1.79 g. of β-(3-phenylureido)ethylamine and 20 ml. of isopropanol is heated under reflux for 3 hours and then cooled and evaporated to dryness under reduced pressure. The residue is suspended in acetic acid and shaken for 30 minutes in the presence of a 30% palladium-on-charcoal catalyst and in an atmosphere of hydrogen, at laboratory temperature and atmospheric pressure, when 255 ml. of hydrogen have been absorbed. The mixture is filtered, the filtrate is evaporated to dryness under reduced pressure and the residue is dissolved in methanol. A solution of oxalic acid in ether is added and the mixture is filtered. The solid residue is crystallised from a mixture of methanol and ether and there is thus obtained 1-p-hydroxyphenoxy 3-β-(3-phenylureido)ethylamino-2-propanol hemioxalate, m.p. 164°–165° C.

The process described above is repeated except that the appropriate 1-benzyloxyphenoxy 2,3-epoxypropane (prepared by conventional means from the corresponding benzyloxyphenol and epichlorohydrin) and the appropriate β-substituted-ethylamine derivative (prepared as hereinbefore described), and there are 1-(p-Hydroxyphenoxy)-3-γ-isobutyramidopropylamino-2-propanol hemioxalate hemihydrate has m.p. 179°–180° C. (crystallised from a mixture of methanol and ether).

EXAMPLE 14 p-Tolyl isocyanate (2.9 g.) is added slowly to a solution of 8.12 g. of 1-p-benzyloxyphenoxy-3-(N-benzyl-N-β-aminoethyl)amino-2-propanol in 50 ml. of toluene which is maintained at laboratory temperature. The mixture is diluted with petroleum ether and filtered and the solid residue is crystallised from a mixture of ethyl acetate and petroleum ether. There is thus obtained 1-p-benzyloxyphenoxy-3-[N-benzyl-N-β(3-p-tolylureido)ethyl]amino-2-propanol.

A solution of 6.55 g. of the above product in acetic acid is shaken with hydrogen in the presence of a 30% palladium-on-charcol catalyst at laboratory temperature and atmospheric pressure until 500 ml. of hydrogen have been absorbed and the uptake of hydrogen ceases. The mixture is filtered, the filtrate is evaporated to dryness and the residue is converted into an oxalate salt which is crystallised from water. There is thus obtained 1-p-hydroxyphenoxy-3-β-(3-p-tolylureido)ethylamino-2propanol hemioxalate, m.p. 173°–174° C. (which contains one quarter of a mole of water of crystallisation).

The 1-p-benzyloxyphenoxy-3-(N-benzyl-N-β-aminoethyl) amino-2-propanol used as starting material may be obtained as follows:

A mixture of 51.2 g. of 1-p-benzyloxyphenoxy2,3-epoxypropane, 51.3 g. of N-benzyl-N-β-isobutyramidoethylamine hydrochloride, 200 ml. of aqueous N-sodium hydroxide solution and 600 ml. of isopropanol is heated under reflux for 17 hours and then evaporated to dryness under reduced pressure. The residue is shaken with a mixture of chloroform and water and the chloroform layer is dried and evaporated to dryness.

The residue is added to a solution of 200 g. of potassium hydroxide in 400 ml. of ethanol and the mixture is heated under reflux for 96 hours and then diluted with water and extracted with ether. The ethereal extract is washed with water, dried and evaporated to dryness. There is thus obtained as oily residue 1-p-benzyloxyphenoxy 3-(N-benzyl-Nβ-aminoethyl)amino-2-propanol which is used without further purification.

EXAMPLE 15

The process described in Example 14 is repeated except that the appropriate isocyanate is used in place of p-tolyl isocyanate. There are thus obtained the compounds described in the following table:

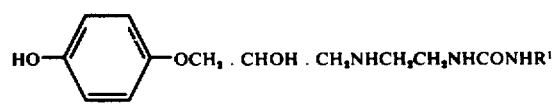

| R¹ | base or salt | m.p. (° C.) | Crystallisation solvent |
| --- | --- | --- | --- |
| isopropyl | hemioxalate hemihydrate | 192–193 (with decomposition) | methanol/water/ether |
| n-butyl | hydrochloride dihydrate | 151–152 | ethanol/ether |
| n-octyl | hydrochloride hemihydrate | 117 | ethanol/ether |
| cyclohexyl | hydrochloride tetrahydrate | 145–150 | ethanol/ether |
| p-methoxyphenyl | hemioxalate hemihydrate | 180–181 | water |

EXAMPLE 16

A mixture of 5.12 g. of 1-m-benzyloxyphenoxy-2,3-epoxypropane, 5.38 g. of N-benzyl-N-β-(3-phenylureido)ethylamine and 50 ml. of isopropanol is heated under reflux for 17 hours, cooled and evaporated to dryness under reduced pressure. The residue is dissolved in acetic acid and shaken for 19 hours in the presence of a 30% palladium-on-charcoal catalyst and in an atmosphere of hydrogen at laboratory temperature and atmospheric pressure, when 830 ml. of hydrogen have been absorbed. The mixture is filtered, the filtrate is evaporated to dryness and the residue is dissolved in ethanol. A solution of oxalic acid in ether is added, the mixture is filtered and the solid residue is crystallised from water. There is thus obtained 1m-hydroxyphenoxy-3-β-(3-phenylureido)ethylamino-2-propanol hemioxalate hemihydrate, m.p. 145°–146° C.

The process described above is repeated except that 1-(3,4-dibenzyloxyphenoxy)-2,3-epoxypropane is used in place of 1-m-benzyloxyphenoxy-2,3-epoxypropane. There is thus obtained 1-(3,4-dihydroxyphenoxy)-3-β-(3-phenylureido)ethylamino-2-propanol hemioxalate, m.p. 122° C. with decomposition (crystallised from isopropanol).

The N-benzyl-N-β-(3-phenylureido)ethylamine used as starting material may be obtained as follows:

Benzaldehyde (13 g.) is added dropwise to a stirred solution of N-β-(3-phenylureido)ethylamine (20 g.) in ethanol (100 ml.) which is maintained at 5° C. The mixture is then stirred for 1 hour at laboratory temperature, ethanol (200 ml.) is added and the mixture is again stirred and cooled to 5° C. Sodium borohydride (5 g.) is added portionwise at this temperature, and the mixture is then stirred for 2 hours at laboratory temperature. Aqueous acetic acid is then added to destroy the excess of sodium borohydride, the mixture is evaporated to dryness under reduced pressure and the residue is suspended in aqueous sodium hydroxide solution. The suspension is extracted with ethyl acetate, and the extract is then shaken with aqueous 2N-hydrochloric acid. The mixture is filtered and the solid residue is washed with water and with ethyl acetate and dried. There is thus obtained N-benzyl-N-β-(3-phenylureido)ethylamine hydrochloride, m.p.165°–166° C.

EXAMPLE 17

The process described in Example 1 is repeated except that the appropriate 2,3-epoxy-1-phenoxypropane and the appropriate β-carboxamidoethylamine are used as starting materials. There are thus obtained the compounds described in the following table:

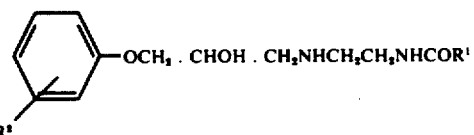

| R¹ | R² | m.p. (° C.) | Crystallisation solvent |
| --- | --- | --- | --- |
| t-butyl | 2-cyano | 152–154 | acetonitrile |
| t-butyl | 2-nitro | 165–166 | acetonitrile |
| isopropyl | 2-allyl | 112–113 | ethyl acetate/cyclohexane |
| isopropyl | 2-allyloxy | 119–120 | ethyl acetate |

EXAMPLE 18

The process described in Example 2 is repeated except that the appropriate 2,3-epoxy-1-phenoxypropane and the appropriate β-sulphonamidoethylamine are used as starting materials. There are thus obtained the compounds described in the following table:

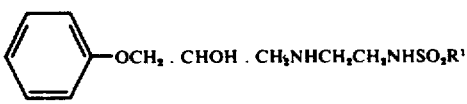

| R¹ | m.p. (° C.) | Crystallisation solvent |
| --- | --- | --- |
| 1-naphthyl | oxalate 199–201 | water |
| 2-tolyl | 153–155 | ethanol |

EXAMPLE 19

The process described in Example 5 is repeated except that the appropriate 2,3-epoxy-1-phenoxypropane and the appropriate β-ureidoethylamine are used as starting materials. There are thus obtained the compounds described in the following table :

[Structure: phenyl—OCH₂.CHOH.CH₂NHCH₂CH₂NHCONHR¹]

| R¹ | m.p. (° C.) | Crystallisation solvent |
|---|---|---|
| H | 108–110 | acetonitrile |
| cyclohexyl | 156–158 | acetonitrile |

EXAMPLE 20

The process described in Example 5 is repeated except that the appropriate 2,3-epoxy-1-phenoxypropane and the appropriate β-amidoalkylamine are used as starting materials. There are thus obtained the compounds described in the following tables :

[Structure: phenyl(R²)—OCH₂.CHOH.CH₂NHCH(CH₃)CH₂NH—X—Y—R¹]

| R¹ | —X—Y— | R² | m.p. (° C.) | Crystallisation solvent |
|---|---|---|---|---|
| phenyl | —COCH₂ | 3-methyl | hydrogen fumarate 87–90 | acetonitrile |
| phenyl | —COCH₂ | 3-bromo | 118–119 | ethyl acetate |
| 2-chlorophenyl | —COCH₂— | 2-nitro | 98–101 | toluene |
| phenyl | —COCH₂ | 3-methoxy | hydrogen fumarate 85–90 | ethyl acetate |
| 2-nitrophenyl | —SO₂— | H | (oil) | — |
| n-butyl | —CONH— | H | (oil) | — |

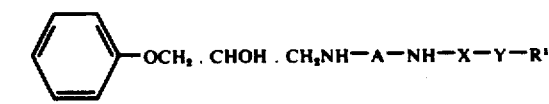

| R¹ | —X—Y— | A | m.p. (° C.) | Crystallisation solvent |
|---|---|---|---|---|
| isopropyl | —CO— | —C(CH₃)₂CH₂— | (oil) | — |
| phenyl | —COCH₂— | —C(CH₃)₂CH₂— | (oil) | — |

| phenyl | —SO₂— | —(CH₂)₁₂— | 86–87 | ethyl acetate |

The compounds isolated only as oils are purified by thick-layer chromatography, and their structures are confirmed by proton magnetic resonance spectroscopy.

The various β-amidoalkylamine derivatives used as starting materials may be obtained by a similar process to that described in the second part of Example 10. Those that are characterised may be obtained as follows :

from 2-nitrobenzenesulphonyl chloride and 1,2-diaminopropane, 1-methyl-2-(2-nitrosulphonamido)ethylamine, m.p. 178°–179° C. after crystallisation from ethanol;

from ethyl isobutyrate and 1,2-diamino-2-methylpropane, 1,1-dimethyl-2-isobutyramidoethylamine (hydrochloride m.p. 269°–270° C. after crystallisation from ethanol);

from ethyl phenylacetate and 1,2-diamino-2-methylpropane, 1,1-dimethyl-2-phenylacetamidoethylamine (hydrochloride m.p. 268°–270° C. after crystallisation from ethanol); from benzenesulphonyl chloride and 1,12-diaminododecane, 12-benzenesulphonamidododecylamine, m.p. 77°–80° C. after crystallisation from a mixture of ethyl acetate and petroleum ether.

EXAMPLE 21

The process described in Example 12 is repeated except that 1-phenoxy-3-β-(2,5-dibenzyloxybenzamido)ethylamino-2-propanol (oxalate m.p. 176°–½° C.; prepared as described in Example 1 from β-(2,5-dibenzyloxybenzamido)ethylamine, m.p. 96°–98° C.) or 1-phenoxy-3-β-(3,4-dibenzyloxybenzamido)-ethylamino-2-propanol (Example 6) is used as starting material. There are thus obtained respectively 1-phenoxy-3-β-(2,5-dihydroxybenzamido)ethylamino-2-propanol (hemioxalate m.p. 195°–197° C. after crystallisation from a mixture of ethanol and water), and 1-phenoxy-3-β-(3,4-dihydroxybenzamido)ethylamino-2-propanol, m.p.178°–180° C. after crystallisation fromm ethanol.

EXAMPLE 22

The process described in Example 13 is repeated except that the appropriate β-substituted ethylamine is used in place of β-(3-phenylureido)ethylamine. There are thus obtained the compounds described in the following table:

| R¹ | —X—Y— | A | m.p. (° C.) | Crystallisation solvent |
|---|---|---|---|---|
| isopropyl | —CO— | —CH₂CH₂— | hemioxalate quarter-hydrate 213 | ethanol |

-continued

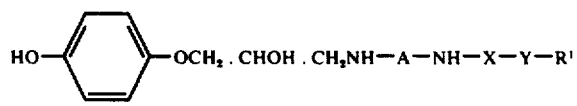

| R¹ | —X—Y— | A | m.p. (° C.) | Crystallisation solvent |
|---|---|---|---|---|
| isopropyl | —CO— | CH₃<br>\|<br>—CH—CH₂— | hemioxalate quarter-hydrate 220 (with decompositon) | water |
| ethyl | —CO—O— | —CH₂CH₂— | hemioxalate 189 | aqueous ethanol |
| methyl | —SO₂— | —CH₂CH₂— | oxalate 119.5–120 | aqueous ethanol |

EXAMPLE 23

The process described in Example 14 is repeated except that the appropriate isocyanate is used in place of p-tolyl isocyanate. There are thus obtained the compounds described in the following table:

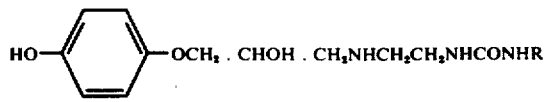

| R | Base or salt | m.p. (° C.) | Crystallisation salt |
|---|---|---|---|
| t-butyl | oxalate hemihydrate | 133–135 (with decomposition) | ethanol/ether |
| o-tolyl | acetate | 109–111 | petroleum ether (b.p.60–80° C.) |
| o-methoxyphenyl | oxalate sesquihydrate | 68–71 (with decomposition) | ethanol |
| 2,4-dimethylphenyl | acetate quarter hydrate | 133–135 | isopropanol |
| 1-naphthyl | hemioxalate | 159–162 | ethanol |
| 4-biphenylyl | hydrate hemioxalate hemihydrate | 211 (with decomposition) | methanol |
| methoxymethyl | oxalate | (hygroscopic) | ethanol/ether |
| n-butyloxycarbonylmethyl | oxalate | (hygroscopic) | — |

EXAMPLE 24

The process described in Example 16 is repeated except that the appropriate 1-benzyloxyphenoxy-2,3-epoxypropane and the appropriate N-benzyl-N-β-amidoethylamine are used as starting materials. There are thus obtained the compounds described in the following table:

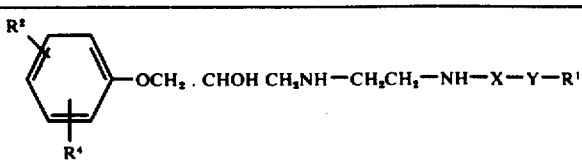

| R¹ | —X—Y— | R² | R⁴ | m.p. (° C.) | Crystallisation solvent |
|---|---|---|---|---|---|
| phenyl | —SO₂— | 3-methoxy | 4-hydroxy | oxalate hemihydrate 127–130 | ethanol |
| phenyl | —CONH— | 3-methoxy | 4-hydroxy | hemioxalate quarter hydrate 167–168 (with decompositon) | water |
| isopropyl | —CO— | 3-hydroxy | 4-hydroxy | hemioxalate 168 (with decomposition) | isopropanol/methanol |
| isopropyl | —CO— | 3-hydroxy | 5-hydroxy | hydrochloride (oil) | — |
| isopropyl | —CO— | 4-hydroxy | 3-hydroxymethyl | hemioxalate hemihydrate 148–149 | ethanol |
| phenyl | —SO₂— | 4-hydroxy | 3-hydroxymethyl | oxalate 117–119 | ethanol |

-continued

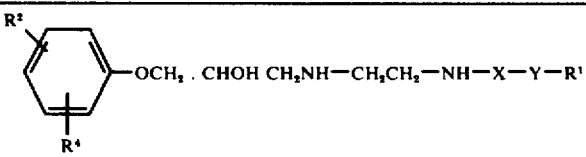

| R¹ | —X—Y— | R² | R⁴ | m.p. (° C.) | Crystallisation solvent |
|---|---|---|---|---|---|
| phenyl | —SO₂— | 3-hydroxy | 4-hydroxy | oxalate hemihydrate 134 (with decomposition) | ethanol/ isopropanol |
| phenyl | —CONH— | 4-hydroxy | 3-hydroxymethyl | hemioxalate hemihydrate 135–137 | methanol/ ether |

The N-benzyl-N-β-amidoethylamine derivatives used as starting material may be obtained by a similar process to that described in the last part of Example 16, from benzaldehyde and the appropriate β-amidoethylamine. N-benzyl-N-β-isobutyramidoethylamine hydrochloride has m.p. 197°–199° C., and N-benzyl-N-β-benzenesulphonamidoethylamine hydrochloride has m.p. 173°–175° C.

EXAMPLE 25

The process described in Example 16 is repeated except that 1-p-benzyloxyphenoxy-2,3-epoxypropane and N-benzyl-N-[1-methyl-2-(3-phenylureido)]ethylamine are used as starting materials. There is thus obtained 1-p-hydroxyphenyl-3-[1-methyl-2-(3-phenylureido)]ethylamino-2-propanol, characterised as the oxalate hydrate m.p. 81° C. (with decomposition) after crystallisation from ethanol.

The N-benzyl-N-[1-methyl-2-(3-phenylureido)]ethylamine used as starting material may be obtained as follows:

A mixture of ethyl phenylcarbamate (50 g.) and 1,2-diaminopropane (105 g.) is heated at 125° C. for 17 hours and cooled, and the excess of amine is removed by evaporation under reduced pressure. The residue is dissolved in ethyl acetate and the solution is washed with saturated brine, dried and evaporated to dryness. The residue is triturated with toluene and there is thus obtained as solid residue 1-methyl-2-(3-phenylureido)ethylamine, which is used without further purification.

Benzaldehyde (6.05 g.) and the above amine (10 g.) are condensed and the product reduced under similar conditions to those described in the last part of Example 16. There is thus obtained N-benzyl-N-[1-methyl-2-(3-phenylureido)] ethylamine, m.p. 118°–120° C. after crystallisation from isopropanol.

EXAMPLE 26

A mixture of dimethylcarbamoyl chloride (2.15 g.), 1-p-benzyloxyphenoxy-3-(N-benzyl-N-β-aminoethyl)amino-2-propanol (8.12 g.), anhydrous potassium carbonate (2.76 g.) and toluene (60 ml.) is stirred at laboratory temperature for 2 hours and then diluted with ethyl acetate. The solution is washed with water, dried and evaporated to dryness and the residue is dissolved in acetic acid. The solution is shaken with hydrogen by a similar process to that described in the second part of Example 14, and there is thus obtained 1-p-hydroxyphenoxy-3-β-(3,3-dimethylureido)ethylamino-2-propanol oxalate hemihydrate, m.p. 181° C. after crystallisation from methanol.

The process described above is repeated except that dimethylsulphamoyl chloride is used in place of dimethylcarbamoyl chloride, and that the dibenzyl intermediate is purified by chromatography, on silica gel using a 1:1 v/v mixture of ethyl acetate and chloroform as eluant, before removal of the benzyl groups of hydrogenolysis. There is thus obtained 1-p-hydroxyphenoxy-3-β-(3,3-dimethylsulphamido)-ethylamino-2-propanol hemioxalate hemihydrate, m.p. 171°–172° C. (with decomposition) after crystallisation from ethanol.

EXAMPLE 27

A solution of 2.1 g. of trifluoroacetic anhydride in 5 ml. of toluene is added during 15 minutes to an ice-cooled solution of 3.0 g. of 1-phenoxy-3-(N-benzyl-N-β-aminoethyl)-amino-2-propanol and 1.01 g. of triethylamine in 30 ml. of toluene and the mixture is stirred for a further 30 minutes and then washed four times with 20 ml. of water each time. The toluene phase is separated, dried over anhydrous magnesium sulphate and evaporated to dryness under reduced pressure. The residue is dissolved in 50 ml. of ethanol and the solution is shaken with hydrogen in the presence of 0.5 g. of a 30% palladium-on-charcoal catalyst at laboratory temperature and atmospheric pressure until 230ml. of hydrogen have been absorbed. The mixture is filtered, the filtrate is evaporated to dryness and the residue is crystallised from a mixture of ethyl acetate and petroleum ether (b.p. 60°–80° C.). There is thus obtained 1-phenoxy-3-β-trifluoroacetamidoethylamino-2-propanol, m.p. 106°–108° C.

The 1-phenoxy-3-(N-benzyl-N-β-aminoethyl)amino-2-propanol used as starting material may be obtained in a similar manner to that described in the third part of Example 14, except that 1-phenoxy-2,3-epoxypropane is used in place of the 1-p-benzyloxyphenoxy-2,3-epoxypropane. There is thus obtained 1-phenoxy-3-(N-benzyl-N-β-aminoethyl)-amino-2-propanol, m.p. 209°–210° C. after crystallisation from ethanol.

EXAMPLE 28

A solution of 3.74 of 1-phenoxy-3-(N-benzyl-N-β-aminoethyl)amino-2-propanol, 0.6 g. of methyl formate and 1.68 g. of sodium bicarbonate in 40 ml. of n-propanol is heated under reflux for 18 hours and then evaporated to dryness under reduced pressure. The residue is shaken with hydrogen by a similar process to that described in Example 27, and there is thus obtained 1-phenoxy-3-β-formamidoethylamino-2-propanol, m.p. 107°–109° C. after crystallisation from ethyl acetate.

EXAMPLE 29

A mixture of 1,2-diaminopropane (44.4 g.) and ethyl acetate (17.6 g.) is heated under reflux for 48 hours and then distilled, the fraction having boiling point 112°–113° C./0.35 mm. being collected. This material is dissolved in acetonitrile (200 ml.) and ethereal hydrogen chloride solution is added. The mixture is filtered and there is thus obtained as solid residue a mixture of the hydrochlorides of N-(2-amino-1-methylethyl)acetamide and N-(2-aminopropyl)acetamide.

Benzenesulphonyl chloride (8.8 g.) is added dropwise during 1 hour to a stirred mixture of the above mixture of hydrochlorides (7.5 g.), water (50 ml.) and sodium bicarbonate (8.4 g.) and the mixture is stirred at laboratory temperature for a further 18 hours and then extracted twice with chloroform (50 ml. each time). The combined chloroform extracts are dried and evaporated to dryness under reduced pressure, and the residue is heated under reflux with aqueous 5N-hydrochloric acid (50 ml.) for 18 hours. The mixture is cooled, washed with chloroform (50 ml.) and then evaporated to dryness under reduced pressure. There is thus obtained as solid residue a mixture of the hydrochlorides of N-(2-aminopropyl)benzenesulphonamide and N-(2-amino-1-methylethyl)benzenesulphonamide.

A mixture of the above mixture of hydrochlorides (2.5 g.), n-propanol (40 ml.), sodium bicarbonate (0.84 g.) and 1-phenoxy-2,3-epoxypropane (1.5 g.) is heated under reflux for 18 hours, cooled and filtered and the filtrate is evaporated to dryness under reduced pressure. The residue is extracted three times with chloroform (30 ml. each time) and the combined extracts are dried and evaporated to dryness. The residue is chromatographed on silica gel plates (20 cm. × 20 cm. × 0.5 mm., Merck Kieselgel GF 60F254) using a 4:1 v/v mixture of chloroform and methanol as developing solvent, and the band having an $R_F$ value of 0.5 is removed from each plate and extracted with methanol. The methanol extract is evaporated to dryness and the residue is reapplied to similar plates. The plates are developed with a 9:1 v/v mixture of chloroform and methanol, and are then re-developed 5 times with this solvent. Two distinct bands are obtained, having $R_F$ values of 0.33 and 0.37, and these bands are separately removed from the plates and extracted with methanol. The methanol extract from the band having $R_F$ 0.33 is evaporated to dryness and the residue is dissolved in ethyl acetate (10 ml.) and added to a solution of oxalic acid (0.4 g.) in ethyl acetate (10 ml.). The mixture is filtered and the residue is crystallised from acetonitrile. There is thus obtained 1-phenoxy-3-(2-methyl-2-benzenesulphonamidoethyl)-amino-2-propanol oxalate, m.p. 122°–123° C.

The methanol extract from the band having $R_F$ 0.37 is evaporated to dryness and there is thus obtained as oily residue 1-phenoxy-3-(1-methyl-2-benzenesulphonamidoethyl)-amino-2-propanol, from which no crystalline salt has been obtained.

EXAMPLE 30

The process described in Example 4 is repeated except that 2,3-epoxy-1-(naphth-1-yloxy)propane and β-2-chlorophenylacetamidoethylamine hydrochloride are used as starting materials. There is thus obtained 1-(naphth-1-yloxy)-3-β-(2-chlorophenyl)acetamidoethylamino-2-propanol, characterised as the hydrochloride salt, m.p. 176°–177° C.

EXAMPLE 31

A solution of 2.8 g. of racemic 1-phenoxy-3-β-isobutyramidoethylamino-2-propanol in 25 ml. of ethanol is added to a solution of 2.9 g. of (−)-2,3:4,6-di-O-isopropylidene-2-keto-L-gulonic acid hydrate in 25 ml. of ethanol and the mixture is kept at 4° C. for 18 hours and then filtered. The solid residue is crystallised four times from 10 ml. of ethanol each time, and there is thus obtained (−)-1-phenoxy-3-β-isobutyramidoethylamino-2-propanol (−)-2,3:4,6-di-1-isopropylidene-2-keto-L-gulonate, m.p. 170°–172° C.

The above salt is stirred with aqueous 2n-sodium hydroxide solution (3 ml.) and the mixture is extracted twice with ethyl acetate (5 ml. each time). The combined extracts are dried through a molecular sieve and are added to a solution of 0.6 g. of oxalic acid in 10 ml. of ethyl acetate. The mixture is filtered and the solid residue is washed with ether. There is thus obtained (−)-1-phenoxy-3-β-isobutyramidoethylamino-2-propanol oxalate, m.p. 148°–150° C. (with decomposition), $\alpha_D^{25}$− 12.0° (c. 7.6% is water).

EXAMPLE 32

A mixture of 1.86 g. of 1-chloro-3-phenoxy-2-propanol, 1.3 g. of β-isobutyramidoethylamine, 40 ml. of n-propanol and 0.84 g. of sodium bicarbonate is heated under reflux for 18 hours, cooled and filtered and the filtrate is evaporated to dryness under reduced pressure. The residue is stirred with 20 ml. of water and the mixture is extracted twice with 20 ml. of chloroform each time. The combined chloroform extracts are dried over anhydrous magnesium sulphate and evaporated to dryness. The residue is crystallised from ethyl acetate and there is thus obtained 1-phenoxy-3-β-isobutyramidoethylamino-2-propanol, m.p. 125°–126° C.

EXAMPLE 33

A mixture of 3.12 g. of 1-chloro-3-β-isobutyramidoethylamino-2-propanol oxalate, 0.94 g. of phenol, 1.6 g. of sodium hydroxide, 5 ml. of water and 30 ml. of isopropanol is heated under reflux for 18 hours, cooled and filtered and the filtrate is evaporated to dryness under reduced pressure. The residue is stirred with 20 ml. of water and the mixture is extracted twice with 20 ml. of chloroform each time. The combined chloroform extracts are dried over anhydrous magnesium sulphate and evaporated to dryness. The residue ;is crystallised from ethyl acetate and there is thus obtained 1-phenoxy-3-β-isobutyramidoethylamino-2-propanol, m.p. 125°–126° C.

The 1-chloro-3-β-isobutyramidoethylamino-2-propanol used as starting material may be obtained as follows:

A mixture of 6.5 g. of β-isobutyramidoethylamine, 3.9 ml. of epichlorohydrin and 60 ml. of isopropanol is stirred at laboratory temperature for 18 hours and is then added to a solution of 6.3 g. of oxalic acid in 100 ml. of ethyl acetate. The mixture is stirred for 30 minutes and filtered and the solid residue is crystallised from 100 ml. of ethanol. There is thus obtained 1-chloro-3-β-isobutyramidoethylamino-2-propanol oxalate, m.p. 129°–130° C.

What we claim is:

1. An alkanolamine selected from compounds of the formula:

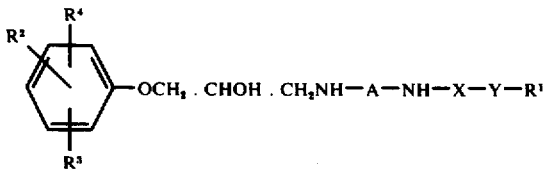

wherein A is alkylene of from 2 to 12 carbon atoms, wherein $R^1$ is hydrogen, or alkyl, halogenoalkyl, alkenyl or cycloalkyl each of up to 10 carbon atoms, or aryl of the formula:

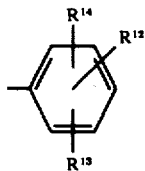

wherein $R^2$, $R^3$, $R^{12}$ and $R^{13}$, which may be the same of different, each is hydrogen, halogen, hydroxy, amino, nitro or cyano, alkyl, cycloalkyl, alkenyl, alkynyl, alkoxy, alkylthio, cycloalkoxy, alkenyloxy, alkynyloxy or alkanoyl each of up to 6 carbon atoms, or aryl, aryloxy or aralkoxy each of up to 12 carbon atoms; or wherein $R^2$ and $R^3$ together, and/or $R^{12}$ and $R^{13}$ together, are trimethylene, tetramethylene, 1-oxotetramethylene, propenylene, but-2-enylene or buta-1,3-dienylene such that together with two adjacent carbon atoms of the benzene ring they form respectively indanyl, 5,6,7,8-tetrahydronaphthyl, 5-oxo-5,6,7,8-tetrahydronaphthyl, indenyl, 5,8-dihydronaphthyl or naphthyl; wherein $R^4$ is hydrogen, hydroxy or hydroxymethyl or aralkoxy of up to 12 carbon atoms; wherein $R^{14}$ is hydrogen, amino or dialkylamino of up to 12 carbon atoms; wherein X is carbonyl (-CO-) and wherein Y is a direct link, or alkylene, oxyalkylene or alkyleneoxy each of up to 6 carbon atoms, or except when $R^1$ is hydrogen is oxygen; and the acid-addition salts thereof.

2. An alkanolamine as claimed in claim 1 selected from compounds of the formula given in claim 1 wherein A is ethylene, trimethylene, tetramethylene, hexamethylene, dodecamethylene, 1-methylethylene, 2-methylethylene or 1,1-dimethylethylene; wherein $R^1$ is hydrogen, methyl, ethyl, n-propyl, isopropyl, n-butyl, isobutyl, t-butyl, n-pentyl, n-octyl, trifluoromethyl, allyl, cyclopropyl, cyclopentyl or cyclohexyl, or aryl of the formula:

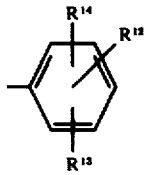

wherein $R^2$, $R^3$, $R^{12}$ and $R^{13}$, which may be the same or different, each is hydrogen, fluorine, chlorine, bromine, iodine, hydroxy, amino, nitro, cyano, methyl, ethyl, n-propyl, cyclopropyl, cyclopentyl, allyl, ethynyl, methoxy, isopropoxy, methylthio, cyclopentyloxy, allyloxy, propargyloxy, formyl, acetyl, phenyl, phenoxy or benzyloxy, or wherein $R^2$ and $R^3$ together and/or $R^{12}$ and $R^{13}$ together are trimethylene, tetramethylene, 1-oxotetramethylene, propenylene, but-2-enylene or buta-1,3-dienylene; wherein $R^4$ is hydrogen, hydroxy, hydroxymethyl or benzyloxy; wherein $R^{14}$ is hydrogen, amino or dimethylamino; wherein X is carbonyl and wherein Y is a direct link, or methylene, ethylene, oxymethylene methyleneoxy, ethyleneoxy, trimethyleneoxy, 1-methylethylideneoxy or 1-methylpropylideneoxy, or except when $R^1$ is hydrogen is oxygen; and the acid-addition salts thereof.

3. An alkanolamine as claimed in claim 1 selected from compounds of the formula given in claim 1 wherein A is ethylene, 1-methylethylene or 1,1-dimethylethylene, $R^1$ is hydrogen, or alkyl, alkenyl or cycloalkyl each of up to 6 carbon atoms, or trifluoromethyl, monohydroxyphenyl or dihydroxyphenyl, Y is a direct link, X is carbonyl, $R^2$ is hydrogen or chloro, cyano, nitro, methyl, allyl, methoxy or allyloxy in the ortho position of the benzene ring and $R^3$ and $R^4$ are both hydrogen; and the acid-addition salts thereof.

4. An alkanolamine as claimed in claim 1 selected from compounds of the formula given in claim 1 wherein A is ethylene, 1-methylethylene or 1,1-dimethylethylene, $R^1$ is phenyl, $R^{12}$ is hydrogen, chloro, nitro, methyl or methoxy, $R^{13}$ and $R^{14}$ are both hydrogen, Y is methylene, ethylene or methyleneoxy, X is carbonyl, $R^2$ is hydrogen or chloro, cyano, nitro, methyl, allyl, methoxy or allyloxy in the ortho- or meta-position of the benzene ring and $R^3$ and $R^4$ are both hydrogen; and the acid-addition salts thereof.

5. The alkanolamine as claimed in claim 1 selected from compounds of the formula given in claim 1 wherein A is ethylene, 1-methylethylene or 1,1-dimethylethylene, $R^1$ is hydrogen or alkyl of up to 6 carbon atoms, Y is methyleneoxy, X is carbonyl, $R^2$, $R^3$ and $R^4$ have the meanings stated in claim 3; and the acid-addition salts thereof.

6. An alkanolamine as claimed in claim 1 selected from compounds of the formula given in claim 1 wherein A is ethylene, 1-methylethylene or 1,1-dimethylethylene, $R^1$ is alkyl or cycloalkyl each of up to 6 carbon atoms or phenyl, $R^{12}$ is hydrogen, methyl, methoxy or phenyl, $R^{13}$ and $R^{14}$ are both hydrogen, Y is a direct link or methylene, X is carbonyl, $R^2$ is hydrogen or hydroxy, $R^3$ is hydrogen and $R^4$ is hydroxy; and the acid-addition salts thereof.

7. An alkanolamine as claimed in claim 1 selected from compounds of the formula given in claim 1 wherein A is ethylene, 1-methylethylene or 1,1-dimethylethylene, $R^1$ is alkyl of up to 6 carbon atoms, Y is oxygen or methyleneoxy, X is carbonyl and $R^2$, $R^3$ and $R^4$ have the meanings stated in claim 7; and the acid-additions salts thereof.

8. An alkanolamine as claimed in claim 1 selected from compounds of the formula given in claim 1 wherein A is ethylene, $R^1$ is phenyl, $R^2$, $R^3$, $R^4$, $R^{12}$, $R^{13}$ and $R^{14}$ are all hydrogen, X is carbonyl and Y is a direct link, or alkylene or alkyleneoxy each of up to 6 carbon atoms, and the acid-addition salts thereof.

9. An alkanolamine as claimed in claim 1 selected from compounds of the formula given in claim 1 wherein A is ethylene, $R^1$ is alkyl, alkenyl or cycloakyl each of up to 6 carbon atoms, $R^2$, $R^3$ and $R^4$ are all hydrogen, X is carbonyl and Y is a direct link; and the acid-addition salts thereof.

10. An alkanolamine as claimed in claim 1 selected from:
  1-phenoxy-3-β-benzamidoethylamino-2-propanol;
  1-phenoxy-3-β-phenylacetamidoethylamino-2-propanol;
  1-phenoxy-3-β-phenoxyacetamidoethylamino-2-propanol;
  1-phenoxy-3-(α-methyl-β-phenylacetamidoethyl)amino-2-propanol;
  1-phenoxy-3-β-pivalamidoethylamino-2-propanol;
  1-phenoxy-3-(β-isobutyramido-α-methylethyl)amino-2-propanol;
  1-(2-nitrophenoxy)-3-β-isobutyramidoethylamino-2-propanol;
  1-phenoxy-3-β-propionamidoethylamino-2-propanol;
  1-phenoxy-3-β-hydroxyacetamidoethylamino-2-propanol;
  1-(2-cyanophenoxy)-3-β-propionamidoethylamino-2-propanol;
  1-phenoxy-3-β-(2-chlorophenylacetamidoethyl)amino-2-propanol;
  1-phenoxy-3-β-butyramidoethylamino-2-propanol;
  1-phenoxy-3-β-isobutyramidoethylamino-2-propanol;
  1-phenoxy-3-β-(4-methoxyphenylacetamidoethyl)amino-2propanol;
  1-phenoxy-3-β-acetamidoethylamino-2-propanol;
  1-(2-methoxyphenoxy)-3-β-isobutyramidoethylamino-2-propanol;
  1-phenoxy-3-(α,α-dimethyl-β-isobutyramidoethyl)amino-2-propanol;
  and 1-phenoxy-3-(α,α-dimethyl-β-phenylacetamidoethyl)amino-2-propanol; and the acid-addition salts thereof.

11. An acid-addition salt as claimed in claim 1 which is a hydrochloride, hydrobromide, phosphate, sulphate, oxalate, lactate, tartrate, acetate, salicylate, citrate, benzoate, β-naphthoate, adipate or 1,1-methylene-bis-(2-hydroxy-3-naphthoate), or a salt derived from a sulphonated polystyrene resin.

12. An alkanolamine as claimed in claim 1 wherein Y is a direct link or alkylene or alkyleneoxy each of up to 6 carbon atoms.

13. An alkanolamine as claimed in claim 1 selected from 1-(2-cyanophenoxy)-3-β-propionamidoethyl amino-2-propanol and the acid-addition salts thereof.

14. An alkanolamine as claimed in claim 1 selected from the group consisting of 1-(3,4-dihydroxyphenoxy)-3-β-isobutyramidoethylamino-2-propanol and the acid-addition salts thereof.

* * * * *